(12) United States Patent
Matsumura

(10) Patent No.: US 7,267,438 B2
(45) Date of Patent: Sep. 11, 2007

(54) FUNDUS PHOTOGRAPHY APPARATUS

(75) Inventor: Kazunori Matsumura, Hamamatsu (JP)

(73) Assignee: Kowa Company Ltd. (JP)

( * ) Notice: Subject to any disclaimer, the term of this patent is extended or adjusted under 35 U.S.C. 154(b) by 24 days.

(21) Appl. No.: 11/353,922

(22) Filed: Feb. 14, 2006

(65) Prior Publication Data
US 2006/0285075 A1 Dec. 21, 2006

(30) Foreign Application Priority Data
Jun. 15, 2005 (JP) ............................. 2005-174445

(51) Int. Cl.
A61B 3/14 (2006.01)
(52) U.S. Cl. .................................... 351/206
(58) Field of Classification Search ........ 351/200–212, 351/221–223
See application file for complete search history.

(56) References Cited

U.S. PATENT DOCUMENTS 6,325,511 B1 * 12/2001 Mizuochi ..................... 351/206
6,779,890 B2 * 8/2004 Matsumoto ................. 351/206

* cited by examiner

Primary Examiner—Hung Dang
Assistant Examiner—M. Hasan
(74) Attorney, Agent, or Firm—Adams & Wilks

(57) ABSTRACT

A fundus photography apparatus is provided that enables optimal adjustment of exposure values according to the color characteristics of the anterior ocular segment of the subject eye. The fundus photography apparatus comprises means for photographing the anterior ocular segment of the eye, means for photographing the eye fundus, and means for detecting the spectral distribution of the iris of the eye based on images of the anterior ocular segment. The photographic exposure value is adjusted in preparation for fudus photography based on the detected spectral distribution of the iris.

6 Claims, 4 Drawing Sheets

FIG. 4

| RING-SLIT | MYDRIATIC (7A) | NON-MYDRIATIC (7B) | FOR SMALL-PUPIL (7C) |
|---|---|---|---|
| | 0 | +1 | +2 |
| MAGNIFICATION | WIDE-ANGLE (LENS 17A) | NARROW-ANGLE (LENS 17B) | |
| | 0 | +1 | |
| MEDIA | ANALOGUE CCD | DIGITAL CCD | |
| | 0 | +3 | |
| IRIS | BROWN | BLUE | |
| | 0 | −1 | |

FUNDUS PHOTOGRAPHY APPARATUS

BACKGROUND OF THE INVENTION

1. Field of the Invention

The present invention relates to a fundus photography apparatus, particularly to an eye fundus photography apparatus equipped with means for photographing the anterior ocular segment of the eye and means for photographing the eye fundus illuminated with a beam of light.

2. Description of the Prior Art

In order for a fundus photography apparatus to obtain good-quality images of the eye fundus, the fundus has to be illuminated with light of optimal intensity during the photography. Doing this requires an automatic exposure mechanism to detect the intensity of light reflected from the fundus and set the exposure accordingly. However, such an automatic exposure mechanism is so complex that generally an optimum reference exposure is set based on the photography conditions, pupil diameter, or past experience of the examiner and he or she corrects the set exposure for eye fundus photography.

When, for example, photography is performed using a high-magnification setting, the reference exposure is greater than when a low-magnification setting is used, and when the fundus camera has a digital type CCD, the reference exposure is greater than when an analogue type device is used.

However, people's eyes are infinitely varied, and the above exposure setting may not provide the best results. One factor in this is that the coloring of the fundus varies from person to person, so the reflectivity also varies. In order to take this into account, the examiner has to check the pupil color of the eye concerned and correct the exposure value based on his or her judgment.

Conventionally, the color has been detected from the fundus image. For example, spectral distribution of a light beam from a specific part of the fundus image is measured and the result is used to calculate and display the color information, as described in Japanese laid open patent publication No. 109032/91. Disclosed in Japanese Patent No. 3363520 is also a method in which the color of the iris is detected and a filter having a prescribed transmission characteristic corresponding to the detected color is selected to emphasize a pattern projected onto the anterior ocular segment of the eye. Japanese laid open patent publication No. 2003-10128 also discloses an arrangement in which the intensity of the observation light source and the gain of means for photographing the observed image are set to desired ones during observation of the anterior ocular segment of the eye.

However, with the conventional fundus photography apparatus, the exposure has to be adjusted according to the color of the iris of the eye, so in order to obtain good-quality fundus images, the examiner has to confirm the color of the eye each time and use his or her judgment to correct the exposure.

The object of the present invention is to provide a fundus photography apparatus that, when photographing an eye fundus, can adjust the exposure to an optimal value depending on the color characteristics of the anterior ocular segment of the eye.

SUMMARY OF THE INVENTION

A fundus photography apparatus according to the present invention comprises means for photographing an anterior ocular segment of a subject eye; means for photographing an eye fundus of the subject eye; means for detecting a spectral distribution of an iris in the anterior ocular segment from a photographed image thereof; and means for adjusting a photographic exposure value based on the detected spectral distribution of the iris when the eye fundus is photographed.

In this invention, the spectral distribution of the iris in the anterior ocular segment of the eye is detected from the image thereof, and the detection results are used as a basis for adjusting the exposure value during photography of the eye fundus. This can prevent overexposure such as in the case of blue eyes, for example, and alleviates the task of correcting the photographic exposure value for different iris colors.

Moreover, the image of the anterior ocular segment can be obtained during alignment prior to photographing the eye fundus, simplifying the adjustment of the exposure value.

Further features of the invention, its nature and various advantages will be more apparent from the accompanying drawings and following detailed description of the invention.

BRIEF DESCRIPTION OF THE DRAWINGS

FIG. 4 is a table showing the factors when setting the photographic exposure value.

DESCRIPTION OF THE PREFERRED EMBODIMENT

The embodiment of the invention will now be described with reference to the accompanying drawings.

Figure 1:
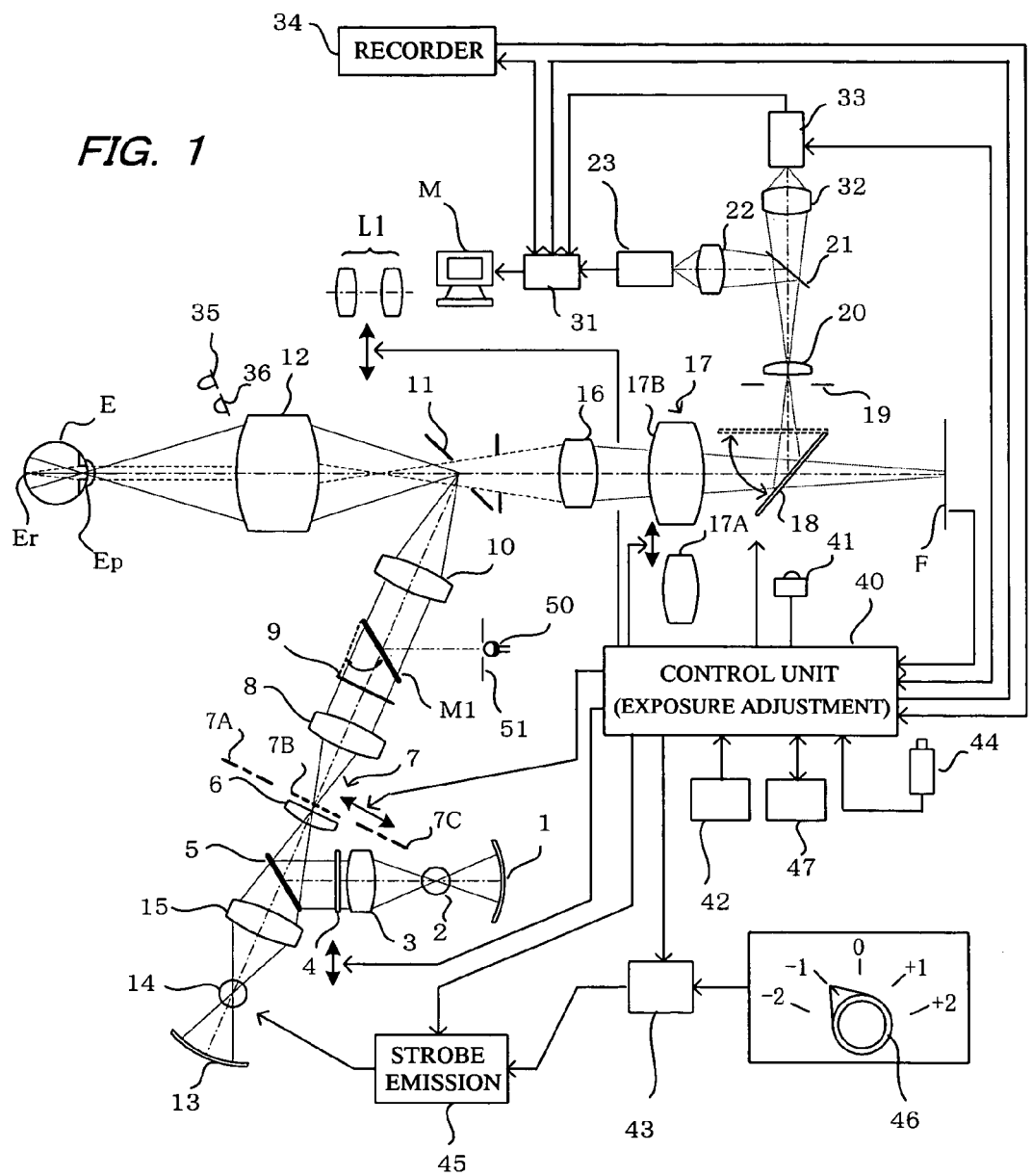
FIG. 1 is a schematic view showing the configuration of the fundus photography apparatus of the present invention.

FIG. 1 shows the configuration of the principal parts that include the optical system of the fundus photography apparatus of the invention. In FIG. 1, an observation light source 2 such as a halogen lamp or the like is located at the focus of a mirror 1. Light from the light source 2 passes via a condenser lens 3, a visible-light cutting and infrared transmitting filter 4, a mirror 5, a lens 6, and impinges on a ring-slit 7 that shapes the light into a ring-shaped beam. The mirror 5 may be a half-mirror, a dichroic mirror (that transmits visible light and reflects infrared light), or a return mirror (retractable mirror). The ring-slit 7 comprises a ring-slit 7A for mydriatic photography, a ring-slit 7B for non-mydriatic photography, and a small-pupil ring-slit 7C, any one of which can be inserted into the optical path depending on the photography mode being used and the eye concerned.

The beam of light that passes through the ring-slit 7 passes through a relay lens 8, a black-point plate 9 for absorbing the reflection of an objective lens 12, a return mirror M1 and a lens 10, and is reflected by an apertured total-reflection mirror 11 disposed at a position that is a conjugate of the position of the pupil Ep at the anterior ocular segment of the subject-eye. The beam of light then passes through the objective lens 12 and the pupil Ep of the eye E, and impinges on the fundus Er.

Light reflected from the fundus Er passes back through the pupil Ep and, via the objective lens 12, passes through a focussing lens 16 and a variable-power lens 17 comprised of lens 17A and 17B, and impinges on return mirror 18.

Depending on the magnification power required, variable-power lens 17A or 17B is inserted into the optical path. Light from the fundus that is reflected at the return mirror 18 passes through a field stop 19 located at the image point, a field lens 20, a dichroic mirror 21 that reflects infrared light and transmits visible light, and a lens 22 to form an image on an imaging device 23. The imaging device 23 is used to photograph moving images and constituted by a CCD or the like that is sensitive to infrared light. Via a switcher 31, the image is displayed on a monitor M, or is recorded by a recorder 34. Thus, when the fundus is illuminated by infrared light, the examiner can use the monitor M to observe the fundus image obtained by the imaging device 23 as a moving image, and can use the recorder 34 to record the moving fundus images.

A visible-light fundus image transmitted by the dichroic mirror 21 passes through the lens 32 and forms an image on an imaging device 33 that is used to photograph still images and constituted by an analogue or digital CCD sensitive to visible light. Via the switcher 31, the image is displayed on the monitor M, or is recorded by the recorder 34. When the examiner operates a shutter switch 44, strobe 14 located at the focal point of the mirror 13 emits light, which passes through the condenser lens 15 and mirror 5 to thereby illuminate the eye fundus Er with visible light. Thus, the examiner can use the imaging device 33 to photograph the fundus as a still image and display it on the monitor M or record it using the recorder 34. Thus, the imaging device 33 functions as means for taking still images of the eye fundus.

When it is required to photograph the fundus on photographic film F, the return mirror 18 is retracted from the optical path in synchronism with the operation of the shutter switch 44, and the fundus image is recorded on the film F.

An auxiliary lens (hereinbelow called an anterior ocular segment lens) L1 can be inserted into the optical path between the total-reflection mirror 11 and the objective lens 12 to observe the anterior ocular segment of the eye. When the anterior ocular segment lens L1 is inserted, an anterior ocular segment illumination and alignment LED 36 emits infrared light that is projected onto the anterior ocular segment to enable alignment to be carried out using the image of the anterior ocular segment. An illumination light source 35 is provided which consists of a low-intensity white-light LED for illuminating the anterior ocular segment. A switch 41 is used to switch on the light source 35 to illuminate the anterior ocular segment. At this time, the imaging device 33 is used to obtain still images of the anterior ocular segment and display the images on the monitor M or record them using the recorder 34. Therefore, the imaging device 33 also functions as means for photographing the anterior ocular segment.

The system is provided with an infrared index light source 50 for projecting a fundus alignment index and an alignment index 51 consisting of a pinhole or the like. The index 51 is projected onto the eye fundus via the return mirror M1.

The fundus photography apparatus is also provided with a control unit 40 comprised of a CPU or the like. According to the photography conditions set by the photography conditions setting unit 42 and the photographic state, the control unit 40 controls the optical path insertion and retraction of the filter 4, the anterior ocular segment lens L1 and the return mirror 18, and also controls the switching of the ring-slit 7 and the variable-power lens 17. The switch 41 is also used to effect short-period activation of the anterior ocular segment illumination light source 35. The control unit 40 also outputs a switching signal to the switcher 31 to switch between displaying the fundus image on the monitor M and recording it on the recorder 34.

In synchronism with the operation of the shutter switch 44, the control unit 40 activates the imaging device 33 and outputs a strobe emission command to a strobe emission circuit 45 and controls the emission intensity of the strobe 14 via a photographic exposure setting unit 43. The intensity of the strobe 14 determines the fundus illumination intensity during fundus photography, which is to say the photographic exposure. The control unit 40 adjusts the exposure according to the photography conditions set by the photography conditions setting unit 42, and outputs the settings to the photographic exposure setting unit 43. Conditions set by the unit 42 include the photography mode, such as mydriatic photography or non-mydriatic photography, the photographic magnification, the type of photographic media (type of imaging device, film, etc.), the eye type, and so forth. Eye type includes information such as whether the eye has a small pupil, and so forth.

The control unit 40 also reads from the recorder 34 anterior ocular segment images obtained by the imaging device 33, and sends the image signals to a spectral distribution detection means 47. The spectral distribution detection means 47 uses the images to detect (analyze) the spectral distribution of the iris, and sends the detection result to the control unit 40, which adjusts the photographic exposure based on the detection result. In this embodiment, the spectral distribution thus detected, meaning the iris color, is used as information relating to the eye type and is included as one of the photography conditions.

The control unit 40 has a default reference exposure value, which is adjusted according to the aforementioned photography conditions and the adjusted exposure value is output to the photographic exposure setting unit 43. The photographic exposure can also be corrected by using dial 46. If necessary, the photographic exposure setting unit 43 sets the photographic exposure after correcting the exposure value output from the control unit 40 by the value indicated by the dial 46. Based on the strobe emission command received from the control unit 40, the strobe emission circuit 45 causes the strobe 14 to emit light at the set exposure level.

Figure 2:
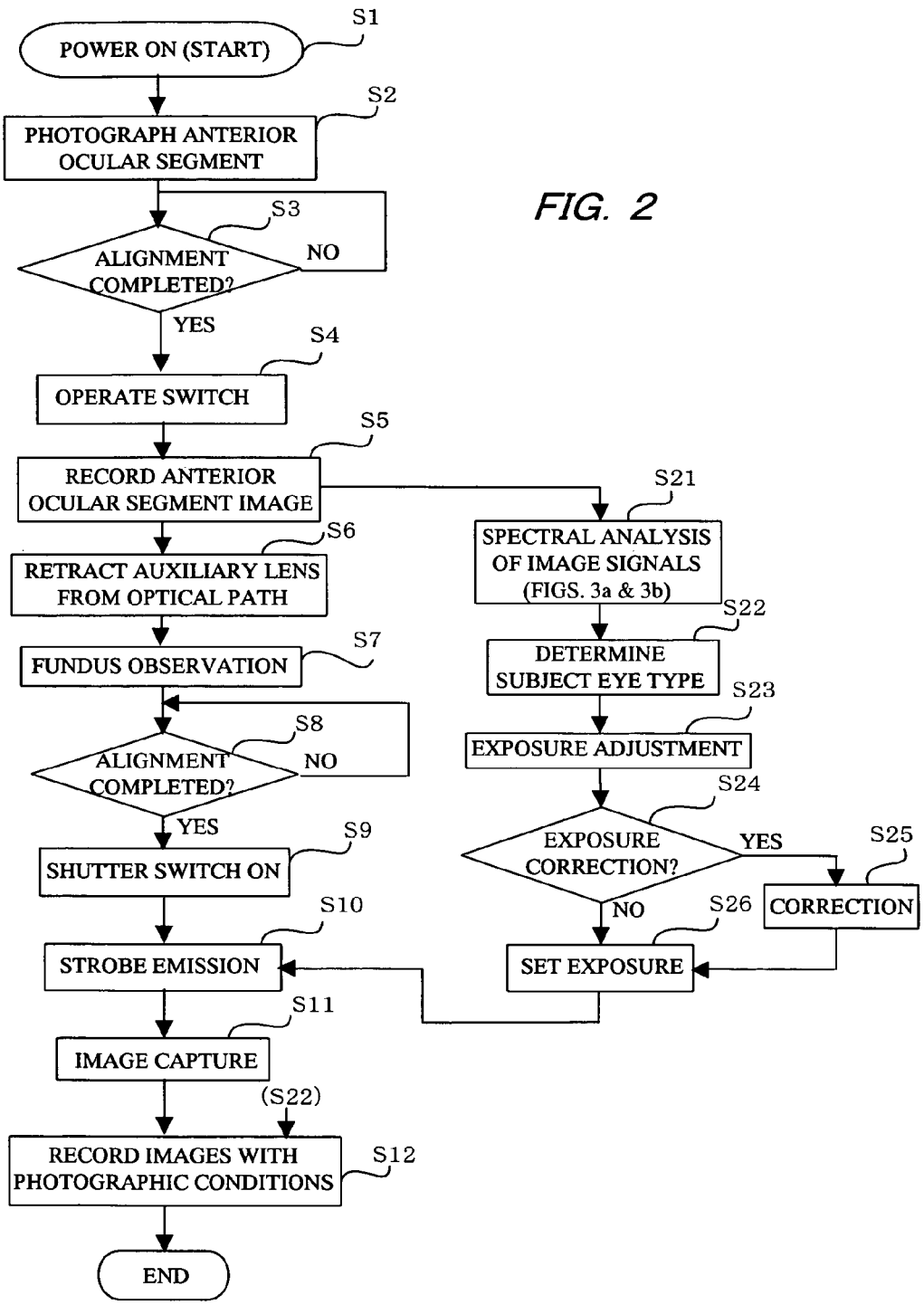
FIG. 2 is a flow-chart of the fundus photography procedure.

The operation of the fundus photography apparatus thus configured will now be described with reference to the flowchart of FIG. 2.

Figure 3A:
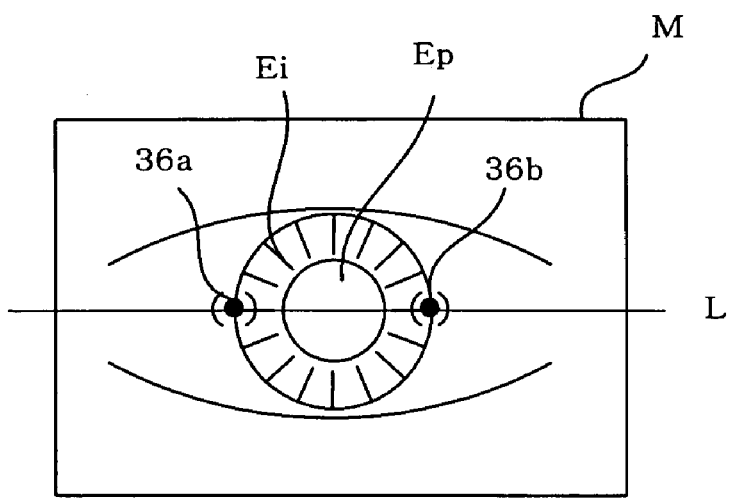
FIG. 3a is a view of an anterior ocular segment image on the monitor screen.

In step S1, the system is initialized to power on, the anterior ocular segment lens L1 is inserted into the optical path and the infrared LED 36 is activated to illuminate the subject eye. Light reflected from the subject eye passes through the objective lens 12, the anterior ocular segment lens L1, the apertured mirror 11 and so forth, is then reflected by the return mirror 18 and by the dichroic mirror 21, and the image is captured by the imaging device 23 with its image displayed on the monitor M (step S2). FIG. 3a shows the anterior ocular segment image displayed on the monitor M, wherein Ep is the pupil and Ei is the iris.

At this time, the infrared LED of the anterior ocular segment index 36 lights, and the system is aligned with the subject eye, using the anterior ocular segment image (step S3). After alignment is completed, a line L connecting the spots 36a and 36b of the index 36 passes substantially through the center of the pupil Ep, as shown in FIG. 3a.

After the alignment, switch 41 is pressed (step S4), causing the illumination light source 35 to come on for a short time during which a visible-light image of the anterior ocular segment is formed on the imaging device 33 and recorded by the recorder 34 (step S5). After that, the light source 35 goes off and the anterior ocular segment lens L1 is retracted from the optical path (step S6). After that, the imaging device 23 can be used to photograph the eye fundus as moving images.

Figure 3B:
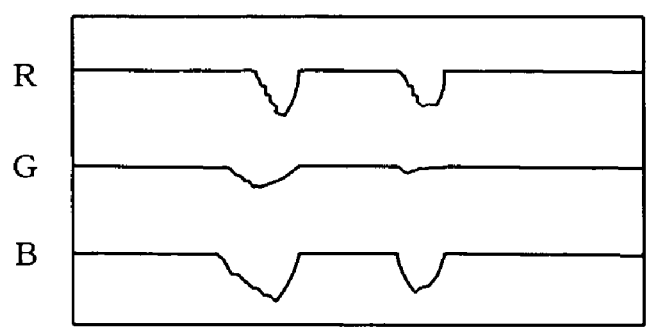
FIG. 3b is an illustrative view showing the analysis of the spectral distribution of the iris.

The anterior ocular segment image recorded in step S5 is read out by the control unit 40 and sent to the spectral distribution detection means 47. The image is then scanned along a prescribed signal line (for example, center line L in FIG. 3a) and subjected to the color separation as shown in FIG. 3b (step S21). With K as the threshold value, the spectral distribution detection means 47 determines that, if $B-\{(R+G)/2\}>K$, the iris Ei is blue, or determines that the iris is brown if K is not exceeded. Alternatively, using K1 and K2 as prescribed threshold values, the spectral distribution detection means 47 determines that the iris Ei is blue when $[B-R>K1]$ and $[B-G>K2]$, and that otherwise the iris is brown. The eye type is thus determined (step S22), and the detection result is output to the control unit 40.

The control unit 40 adjusts the photographic exposure value in accordance with the spectral distribution of the iris, other information on the subject eye, and the conditions set by the photography conditions setting unit 42 (step S23). Examples of photography conditions are shown in the table of FIG. 4. In the table, ring-slit selection (ring-slit 7A, 7B or 7C), photographic magnification (variable-power lens 17A or 17B), and media (whether the imaging device 33 is an analogue or digital CCD) are set by the photography conditions setting unit 42. The iris of the subject eye is the result of the determination of step S22. The control unit 40 adjusts the default reference exposure (zero) in accordance with this table (step S23) and outputs the setting to the exposure setting unit 43.

At this time, the examiner can use the exposure correction dial 46 to make a correction to the exposure value. If the dial 46 is set at something other than zero (YES in step S24), the exposure setting unit 43 corrects the exposure value accordingly (step S25), and the emission intensity of the strobe 14 is set (step S26) in preparation for the actual operation of the shutter switch 44.

When the anterior ocular segment lens L1 is retracted from the optical path (step S6), the infrared fundus image is captured by the imaging device 23 and displayed on the monitor M, enabling the fundus observation (step S7). Then, the examiner makes finer adjustments of the alignment of the system with the eye, using the alignment index 51 while observing the fundus image. When the alignment is done (step S8), the shutter switch 44 is pressed (step S9), the strobe 14 emits light at the exposure intensity set in step S26 (step S10), and the fundus image is captured by the imaging device 33 as a still image (step S11) and recorded in the recorder 34. At this time, iris color and other information about the photography condition settings is associated with the fundus images and displayed or recorded (step S12).

What is claimed is:

1. A fundus photography apparatus comprising:
   means for photographing an anterior ocular segment of a subject eye;
   means for photographing an eye fundus of the subject eye;
   means for detecting a spectral distribution of an iris in the anterior ocular segment from a photographed image thereof; and
   means for adjusting a photographic exposure value based on the detected spectral distribution of the iris when the eye fundus is photographed.

2. An apparatus according to claim 1, further comprising means for displaying or recording the detected results as photography conditions.

3. An apparatus according to claim 1, further comprising means for correcting the exposure value adjusted based on the detected spectral distribution of the iris.

4. A fundus photography apparatus comprising:
   first means for photographing an anterior ocular segment of a subject eye as a still image;
   means for photographing an eye fundus of the subject eye;
   means for detecting a spectral distribution of an iris in the anterior ocular segment from a photographed still image thereof;
   means for adjusting a photographic exposure value based on the detected spectral distribution of the iris when the eye fundus is photographed;
   second means for photographing the anterior ocular segment as a moving image; and
   means for controlling the first means to enable the still image photography of the anterior ocular segment to detect the spectral distribution of the iris during moving image photography by the second means.

5. An apparatus according to claim 4, wherein the second means are used to photograph the eye fundus as a moving image after the anterior ocular segment has been photographed by the first means.

6. An apparatus according to claim 5, wherein an anterior ocular segment lens is provided, which is inserted into the optical path to enable the moving image photography of the anterior ocular segment and is retracted therefrom to enable the moving image photography of the eye fundus.

* * * * *